(12) United States Patent
Martel (10) Patent No.: US 6,720,989 B2
(45) Date of Patent: Apr. 13, 2004

(54) SYSTEM AND METHOD FOR AUTOMATICALLY INSPECTING AN ARRAY OF PERIODIC ELEMENTS

(75) Inventor: Thomas Joseph Martel, Dewitt, NY (US)

(73) Assignee: K-G Devices Corp., Dewitt, NY (US)

( * ) Notice: Subject to any disclaimer, the term of this patent is extended or adjusted under 35 U.S.C. 154(b) by 360 days.

(21) Appl. No.: 09/729,316

(22) Filed: Dec. 5, 2000

(65) Prior Publication Data

US 2001/0033328 A1 Oct. 25, 2001

Related U.S. Application Data

(63) Continuation-in-part of application No. 09/552,685, filed on Apr. 19, 2000, now Pat. No. 6,459,448.

(51) Int. Cl.⁷ .................................. H04N 7/18
(52) U.S. Cl. ........................ 348/92; 348/125
(58) Field of Search ............ 348/88, 92, 125; 382/141–152; 356/237.1–237.6, 238.1, 239.3, 429–430; 250/559.04, 559.08; 702/35; H04N 7/18

(56) References Cited

U.S. PATENT DOCUMENTS

| | | | |
|---|---|---|---|
| 4,498,779 A | 2/1985 | Southgate et al. | 356/384 |
| 4,969,198 A | * 11/1990 | Batchelder et al. | 382/147 |
| RE33,956 E | * 6/1992 | Lin et al. | 250/550 |
| 5,150,175 A | * 9/1992 | Whitman et al. | 356/429 |

(List continued on next page.)

FOREIGN PATENT DOCUMENTS

| | | |
|---|---|---|
| EP | A1 0 300 572 | 1/1989 |
| WO | WO 98/01746 | 1/1998 |

OTHER PUBLICATIONS

G. A. W. West et al., "Image processing and understanding for automatic inspection", Trans Inst M C vol. 10, No. 5, Oct.–Dec. 1988.

(List continued on next page.)

*Primary Examiner*—Young Lee
(74) *Attorney, Agent, or Firm*—Morgan Lewis & Bockius LLP (57) ABSTRACT

The present invention relates to a system and method for scanning electronically acquired periodic images from an object and thereafter, inspecting the periodic images by using predetermined rules. The method to inspect the image includes an algorithm for analyzing the periodic patterns of the image and detecting deviations from numerical acceptance norms. In the system, the field of view of a camera, such as a video camera, viewing the object includes a two-dimensional image of the object. The camera captures the two-dimensional image of the object and converts the image into an array of scan lines, whereby each scan line represents a one-dimensional "slice" of target shape of the object. Hence, while all two dimensional images do not have periodic pattern, the array of scan lines represents a periodic pattern that is used by the algorithm in the inventive system. Alternatively, the camera may capture a scan line of a one-dimensional image with period elements, whereby the scan line represents a one-dimensional slice of target shape. Each slice is broken down into "segments" consisting of sets of adjacent pixels that are similar in brightness, hue, or both. The camera, in conjunction with processing by ancillary electronic data processing means and methods, delivers the slices with segments to the system where they are sequenced. The system identifies every slice and segment to determine what feature of the target shape the slice and segment represent. Thereafter, predefined rules are used to determine if each identified segment deviates from numerical acceptance norms. The method is thus used to analyze periodic elements of any arbitrary target shape, thereby working in a range of different object acceptance norms and being easily adaptable to change from one set of norms to another.

39 Claims, 6 Drawing Sheets

U.S. PATENT DOCUMENTS

| | | | |
|---|---|---|---|
| 5,177,559 A | * 1/1993 | Batchelder et al. | 356/237.5 |
| 5,184,190 A | 2/1993 | Rai et al. | 356/239 |
| 5,463,462 A | * 10/1995 | Ohnishi et al. | 356/521 |
| 5,917,935 A | * 6/1999 | Hawthorne et al. | 382/149 |
| 5,995,137 A | * 11/1999 | Yamada et al. | 348/88 |
| 6,072,900 A | 6/2000 | Chiu et al. | 382/149 |
| 6,459,448 B1 | * 10/2002 | Martel | 348/125 |
| 2002/0052700 A1 | * 5/2002 | Shakespeare | 702/35 |

OTHER PUBLICATIONS

T. Pavlidis, "Algorithms for graphics and image processing" Rockville, Computer Science Press, US pp. 65–71, 142-1–155.

Hans Burthardt et al., "Effiziente Parallelisierung von Algorithmen der digitalen Bildverarbeitung und Mustererkennung" IT + TI Informationstechnik Und Technische Informatik, Oldenbourg Verlag. Munchen, De, vol. 37 No. 2, Apr. 1, 1995.

E. R. Williams, "Two Dimensional Image Sensor Using One Dimensional Sensor Array" Jul. 1978, IBM Technical Disclosure Bulletin, vol. 21, No. 2, pp. 436–437.

D. Snyers et al., "Image processing optimization by genetic algorithm with a new coding scheme" Pattern Recognition Letters, North–Holland Publ. Amsterdam, Nl, vol. 16, No. 8, Aug. 1, 1995, pp. 843–848.

* cited by examiner

FIG. 1A IMAGE WITH SCAN LINE
FIG. 1B ROW SCANNED, SHOWN IN ISOLATION
FIG. 1C ROW SCANNED, POSITIONS ADJUSTED (SEE TEXT)
FIG. 1D RESULTING COMPOSITE IMAGE

SYSTEM AND METHOD FOR AUTOMATICALLY INSPECTING AN ARRAY OF PERIODIC ELEMENTS

RELATED INVENTIONS

This application is a continuation-in-part of U.S. patent application Ser. No. 09/552, 685 filed on Apr. 19, 2000 U.S. Pat. No. 6,459,448.

FIELD OF THE INVENTION

This invention relates to a computer system for inspecting objects for manufacturing defects and more particularly to an algorithm in the computer system for inspecting and analyzing periodic arrays of electronically acquired imagery of an object.

BACKGROUND OF THE INVENTION

While advances in computer processing power have made processing of large amounts of data possible, an automated optical inspection problem for arrays of geometric targets still exists. Automated optical inspection is the inspection of electronically acquired imagery of an object for tolerance, color, blemishes, cracks or a wide variety of manufacturing defects that might be present in the object. The automated optical inspection problem arises, among other places, in the inspection of aperture masks used in CRT-type color monitors and television sets. Problems encountered during aperture masks inspections also occur during inspections of other objects, which include inspection of periodic arrays of annular targets. Thus, two seemly different objects, such as flat panel displays and filters for filtering bacterial particles out of a product stream of bio-engineered vaccines and chemicals have the same inspection problem. Therefore, while the following discusses inspection of aperture masks with arrays of annular targets, it should be apparent to one of ordinary skill in the art that the invention relates to inspection of all objects with arrays of geometric targets.

Aperture masks generally are comprised of thin metal sheets perforated by hundreds of thousands of tiny holes. These holes are too small to see with an unaided eye and each hole has a precise shape, or profile. The shape of each hole varies slightly and definitely according to its position across the width and/or height of the mask. The degree to which the shape of these holes can be maintained in manufacturing of the aperture mask has a direct bearing on whether the mask can be used by a manufacturer.

Inspection of aperture masks during manufacturing is a particularly demanding problem because there are vast numbers of holes, at least several hundred thousand holes, in each mask. Aperture masks are relatively inexpensive to manufacture. Nonetheless, the shape of a single hole that is out of tolerance eventually shows up as a blemish that an end user can see in a finished product. For example, the end user will see a blemish in an image that is produced by a CRT-type color monitor, which includes the defective aperture mask. Thus, automated or manual inspection of each mask has to be performed. Automated inspection by a computer leads to a formidable data reduction problem since each hole must be covered by many pixels, thereby producing billions of pixels across the length and width of each mask.

Some manufacturers use human inspectors to manually inspect each mask but do not use any special magnification method. The human inspectors hold each mask up to the light and bend it in various ways to detect an irregular hole or area in the mask. While the manufacturing of the aperture masks is automated, inspections of the masks are performed by groups of inspectors. Each person in a group may inspect a particular section of the masks and inspections of the masks are performed at much slower rates than the rates at which the masks are manufactured. The manual inspection process also is a relatively expensive undertaking for the manufacturer.

A current automated method uses two-dimensional video cameras to analyze data on a computer. Thereafter various mathematical operations, such as edge detection, a gradient calculation, or some other type of transform to manipulate the data, are performed on the two-dimensional representation of the data. The automated method measures the inside and outside diameter of each hole to calculate whether the inner diameter is the right range of tolerance. This method generates an unusable and impractical amount of data that may only be analyzed by a very specialized and expensive computer. In an industrial environment, the masks vibrate as they emerge from the production line. This vibration is enough to make an image useless unless the image is taken over an extremely short time period.

U.S. patent application Ser. No. 09/522,685 of which this application is a continuation-in-part, relates to a system and method for inspecting electronically acquired imagery, from a one-dimensional camera, of an object for tolerance, color, blemishes, cracks or a wide variety of manufacturing defects that might be present in an object. The method to detect manufacturing defects includes an algorithm for analyzing the periodic pattern of geometric elements in an array and detecting deviations from numerical acceptance norms, such as diameter, spacing, and symmetry, for the geometric elements.

This previously filed application, moreover, discloses a method for analyzing one-dimensional image data. The process of analyzing two-dimensional images, however, is useful in fields of failure analysis and prediction, process control, machine vision and automated optical inspection, and voice recognition (especially in the presence of "noise", data compression, vibration control and echo suppression). What is needed, therefore, is an automated algorithm for inspecting imagery of any one or two-dimensional object that can be implemented by means for parallel hardware scales at a favorable rate with limited inter-processor communication. The method must also be unaffected by the visual effects of mechanical vibration on an image while tolerating the effects of imperfect positions of the target object by an operator or as a result of equipment shortcomings.

SUMMARY OF THE INVENTION

The present invention relates to a system and method for scanning electronically acquired periodic images from an object and thereafter, inspecting the periodic images by using predetermined rules. The method to inspect the image includes an algorithm for analyzing the periodic patterns of the image and detecting deviations from numerical acceptance norms. In the system, the field of view of a camera, such as a video camera, viewing the object includes a two-dimensional image of the object. The camera captures the two-dimensional image of the object and converts the image into an array of scan lines, whereby each scan line represents a one-dimensional "slice" of target shape of the object. Hence, while all two dimensional images do not have periodic patterns, the array of scan lines represent a periodic pattern that is used by the algorithm in the inventive system.

Alternatively, the camera may capture a scan line of a one-dimensional image with periodic elements, whereby the scan line represents a one-dimensional slice of target shape.

Each slice is broken down into "segments" consisting of sets of adjacent pixels that are similar in brightness, hue, or both. The camera, in conjunction with processing by ancillary electronic data processing means and methods, delivers the slices with segments to the system where they are sequenced. The system identifies every slice and segment to determine what feature of the target shape the slice and segment represent. Thereafter, predefined rules are used to determine if each identified segment deviates from numerical acceptance norms. The method is thus used to analyze periodic elements of any arbitrary target shape, thereby working in a range of different object acceptance norms and being easily adaptable to change from one set of norms to another.

The algorithm used in the inventive method accomplishes at least two outcomes simultaneously. It serves as a framework for the transformation of a set of measurements that could be made on a two-dimensional image of the target area into a set of measurements made only on the one-dimensional data set. In addition, the algorithm is capable of accurately measuring a lattice constant, i.e., the spacing between the geometric elements of an array that arises from a data set only after certain manipulations have been made. The lattice constant can be measured without prior knowledge of any scan line other than the one currently being observed. Thus, it is never necessary to assemble a two-dimensional depiction of the one-dimensional video data. This is important in a design of computational hardware to analyze the video data stream generated by any camera, such as a one-dimensional camera or a two-dimensional camera.

Specifically, in a preferred embodiment, the algorithm is used to inspect any array of periodic elements. The inventive method uses predefined rules, whereby not all possibilities in the analysis work. For example, rules may include a pattern rule, derived from the geometry of the scanned elements, a lattice constant rule for estimating the spacing between periodic elements of an array, and an inference rule for analyzing a two-dimensional image. It should be noted that other rules may be used in inspecting and analyzing arrays of periodic elements.

For two-dimensional images, the video camera captures an image of the object and converts the captured image into an array of one-dimensional scan lines of target shape of an object. For one-dimensional images, the video camera captures a single one-dimensional scan line of target shape of an object. First, each scan line data is reduced to a collection of numbers, each representing the brightness of a particular pixel, to "run-length encoded" data. In an embodiment of the invention, the system reduces the scan line data to black and white images by determining if the data is darker or brighter than a predefined threshold. Thus, each pixel in the scan line is reduced to a single bit in the system. As would be apparent to one of ordinary skill in the art, there are other ways of reducing the data to binary data. A consecutive set of all dark or white pixels in a scan line is thus defined as a run. In an alternate embodiment, the system works on data represented in non-binary formats. For example, the system will work with multi-color data encrypted by three or more bits or with analog data in a numeric form.

In a preferred embodiment, the system thereafter generates a set of run-length integers from the reduction of the scan line data. The algorithm implemented in the inventive method applies a technique of search to analyze run-length data derived from each scan line data. Using predefined rules, the system systematically accounts for every possible interpretation of each of the run-length integers, whereby each interpretation is systematically tested using the above mentioned rules and those interpretations that cannot be valid are ignored. When an interpretation is deemed to be invalid, any more extensive interpretation, of which this is only a part, is likewise invalid, and further processing power need not be expended to check it. Thus, the inventive method is used to detect manufacturing defects by detecting paths that deviate from numerical acceptance norms for the periodic elements.

A symbolic designation is assigned to each run. In one embodiment of the invention, symbolic designations under dark runs, in the aperture mask inspection, include a sliver (SLIV), an entry vertical (NV), and an exit vertical (XV) and symbolic designations under light runs include "LAND" and "HOLE". SLIV is the designation used when the scan line passes through the dark sections on the top or bottom of a ring. Entry vertical is the designation used when the scan line passes through the dark section on the right of the center of the hole. Exit vertical is the designation used when the scan line passes through the dark section on the left of the center of the hole. HOLE is the designation used when the scan line passes through the light center of the hole and LAND is the designation used when the scan line passes through the light section outside of the hole. It should be noted that other designations may be made in other applications of the inventive system.

As would be apparent to those of ordinary skill in the art, rules used in the inventive method may be modified as long as there are enough defined rules to keep the systematic accounting of every possible interpretation from growing out of bounds and as long as the inspection problem is computable. That is, each path created from the systematic accounting of every possible interpretation in a scan line can be computed in the system, in parallel by multiple simple processors at very high speed.

It is therefore an object of the invention to provide a system and method for inspecting electronically acquired imagery by converting the image into an array of one-dimensional "slices" of the target shape with every line the camera scans. The method includes means for breaking down each slice into segments, identifying every segment to determine what feature of the target shape the segment represents, sequencing each segment and using rules, to determine if each identified segment deviates from numerical acceptance norms for an annular element.

It is another object of the invention to provide a method for transforming a set of measurements that could be made on a two-dimensional image of the target area into a set of measurements made only on the one-dimensional data set.

It is another object of the invention to provide a method for using rules to analyze the periodic elements or arrays, whereby not all possibilities in the analysis work. The rules in the inventive method can be made to work even when the camera alignment is accidental.

It is another object of the invention to provide a system and method for producing integers from the reduction of the scan line data, whereby a collection of numbers each representing the brightness of a particular pixel results in "run-length encoded" data.

It is another object of the invention to provide a technique or search method for systematically accounting for every possible interpretation of each of the run-length integers and ignoring those interpretations that cannot be valid.

It is yet another object of the invention to provide a computational system and method for analyzing every possible interpretation of each of the run-length integers in parallel.

Additional features and advantages of the invention will be set forth in the description that follows, and in part will be apparent from the description, or may be learned by practice of the invention. The objectives and advantages of the invention will be realized and attained by the system particularly pointed out in the written description and claims hereof as well as the appended drawings.

To achieve these and other advantages and in accordance with the purpose of the invention, as embodied and broadly described, the present invention provides a method in a system for using electronically acquired imagery of an object to inspect the object for a wide variety of manufacturing defects, the method comprising the steps of: capturing, by a capturing means, an image of the object and converting the image into an array of periodic elements; delivering the array of periodic elements to a computer system for sequencing; reducing each periodic element into segments consisting of sets of similar adjacent pixels; systematically accounting for all possible interpretations of each run using a plurality of predefined rules to determine deviations from a set of acceptance norms for the array of periodic elements; and systematically testing each interpretation wherein invalid interpretations are ignored.

The invention also provides a system for using electronically acquired imagery of an object to inspect the object for a wide variety of manufacturing defects, the system comprising: a capturing means for electronically capturing an image of the object and converting the image into an array of periodic elements; means for delivering the array of periodic elements from the capturing means to a computer system; and software means in the computer system for processing and reducing the array of periodic elements to a plurality of run-length integers whereby each run-length integer represents one run, systematically accounting for all possible interpretations of each run using a plurality of predefined rules to determine deviations from a set of acceptance norms for the array of periodic elements, systematically testing each interpretation, and ignoring invalid interpretations.

The invention also provides a software component in a computer system for inspecting electronically acquired imagery of an object for a wide variety of manufacturing defects, the software component comprising: first processing mean for processing and reducing an array of periodic elements to a plurality of run-length integers whereby each run-length integer represents one run; second processing means for systematically accounting for all possible interpretations of each run using a plurality of predefined rules to determine deviations from a set of acceptance norms for the array of periodic elements; and third processing means for systematically testing each interpretation and for ignoring invalid interpretations.

The invention also provides a system for using electronically acquired imagery of an object to inspect the object for a wide variety of manufacturing defects, the system comprising: a capturing means for electronically capturing an image of the object and converting the image into an array of periodic elements; means for delivering the array of periodic elements from the capturing means to a computer system; and software means in the computer system for processing and reducing the array of periodic elements to a plurality of run-length integers whereby each run-length integer represents one run, for systematically accounting for all possible interpretations of each run using a plurality of predefined rules to determine deviations from a set of acceptance norms for the array of periodic elements, systematically testing each interpretation, and ignoring invalid interpretations; and a plurality of simple processors for parallel processing of a plurality of interpretations at very high speed.

BRIEF DESCRIPTION OF THE DRAWINGS

The accompanying drawings, which are included to provide a further understanding of the invention and are incorporated in and constitute a part of this specification, illustrate embodiments of the invention that together with the description serve to explain the principles of the invention.

In the drawings:

FIG. 1-A illustrates a two-dimensional image obtained from a two-dimensional camera, where the horizontal black line represents a one-dimensional "scan line;"

FIG. 1-B illustrates a row of annular elements, from FIG. 1-A, as shown in isolation;

FIG. 1-C illustrates a row of annular elements having vertical position adjustments;

FIG. 1-D illustrates a resulting composite image from FIG. 1-A;

DETAILED DESCRIPTION

Reference will now be made in detail to the preferred embodiments of the present invention, examples of which are illustrated in the accompanying drawings. The present invention described below extends the functionality of the inventive method for inspecting objects with periodic elements.

In the invention, electronically acquired imagery of an object, from a one-dimensional video camera, is inspected for tolerance, color, blemishes, cracks or a wide variety of manufacturing defects that might be present. As would be apparent to one skilled in the art, electronic imagery may be acquired by other scanning means, such as flying-spot scanner, scanning electron microscopes, scanning tunneling microscopes and atomic force microscopes. Equipment for one-dimensional video imaging is less expensive per unit of performance than is equipment for two-dimensional video imaging, and it is easier to illuminate a line target than an area target. Moreover, one-dimensional data is collected over a much smaller time-scale than two-dimensional video data. This advantage is likely to increase over time since technical improvements in two-dimensional technology will be applicable to one-dimensional equipment. The system using a one-dimensional camera also detects every flaw detected by systems operating on two-dimensional data from conventional two-dimensional cameras.

Specifically in the invention, a one-dimensional video camera, such as a line scan camera, captures a single one-dimensional "slice" of target shape with every line it scans. Each slice is broken down into "segments" consisting of sets of adjacent pixels that are similar in brightness, hue, or both. An algorithm used in the inventive method identifies every segment to determine what feature of the target shape the segment represents. Rendering of the target shape into features may be accomplished using techniques for automatically resolving a physical object into finite elements for stress or thermal analysis. As segments are delivered into the system by the line scan camera, the segments are sequenced, and predefined rules are used to determine whether a particular identity assignment accurately reflects numerical acceptance norms. The inventive method is thus able to analyze periodic arrays of any arbitrary target shape, and the effectiveness of the system actually improves for more complex target shapes. As long as the rules used when implementing the method keep the number of choices from growing without bound, the system is able to locate at least one set of labels in which every segment has exactly one label, which "explains" the segment.

FIGS. 1-A to 1-D illustrate a progression of different depictions of the same data and they are used to illustrate how the algorithm in the inventive method functions. FIG. 1-A illustrates an image 100, which is a two-dimensional depiction of a region covered by an array of annular rings 102. Horizontal black line 104 is intended to show the locus of all points covered by a single scan line derived from a one-dimensional video camera that is positioned so as to observe the ring pattern. FIG. 1-B illustrates a scan line 106, from FIG. 1-A, as shown in isolation. Scan line 106 shows only those rings that are near, or in contact with horizontal black line 104. Since the rings that are not proximate to horizontal line 104 cannot be seen by the one-dimensional camera, they do not contribute any data to scan line 106. Thus, nothing is changed when they are omitted from the picture. FIG. 1-C illustrates scan line 108, from FIG. 1-B, which is adjusted. Specifically, the rings in adjusted scan line 108 are displaced vertically in order to bring them into horizontal alignment. As each ring is displaced, the segment of the scan line that is in the neighborhood of the ring is also moved in order that the data produced by the scan line not be altered. The act of "breaking" up the scan line between FIG. 1-B and FIG. 1-C implies that "break points" are evenly spaced along the length of the line, with the interval of spacing equal to the lattice constant of the imaged ring array. The lattice constants are spacing between annular elements 102 of the array that arises from the data set only after certain manipulations have been made. By knowing the element spacing, the two-dimensional analysis problem can be transformed into a one-dimensional analysis problem, at least for arrays of identical objects.

FIG. 1-D illustrates a resulting composite 110 image from FIG. 1-A, whereby the dark and light segments arising from the scan line are stacked vertically. By so doing, a composite image of what appears to be a single annulus is created. Composite image 110 is created from data taken from the collection of all seventeen annuli 102 that are seen by the camera. The two-dimensional "composite" representation 110 of the data is the result of the angular displacement between the axis of the scan line and the major axis of symmetry of the array pattern. This displacement gives rise to a scanning phenomenon that enables the system to re-create an apparently two-dimensional image of a single annulus. If the scan line is perfectly aligned with one or another symmetry axis of the array, the scanning behavior will not be seen. Thus, there are certain forbidden/accidental orientations of the line-scan camera at which an algorithm implemented in the inventive method will not work as well. In practice the range of forbidden orientations is small when compared to the total number of possible orientations and alignments that can occur between a physical camera and a physical annulus array. Nevertheless, the analytical technique implemented in the inventive method can be made to work even when the camera alignment is "accidental;" however, a different set of measurement parameters must be brought to play. In most cases, these accidental situations can be "detected" by the method for inspecting the image.

Figure 1A:
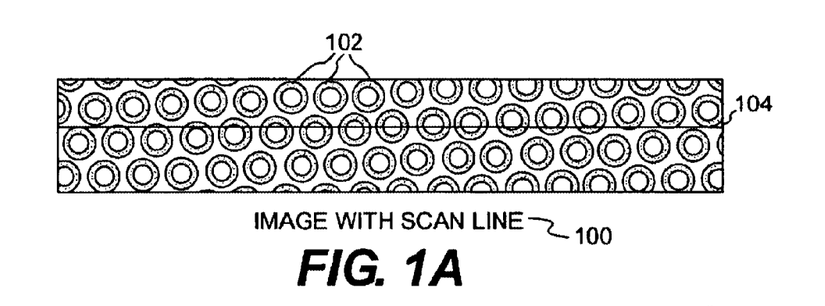
Figure 1B:
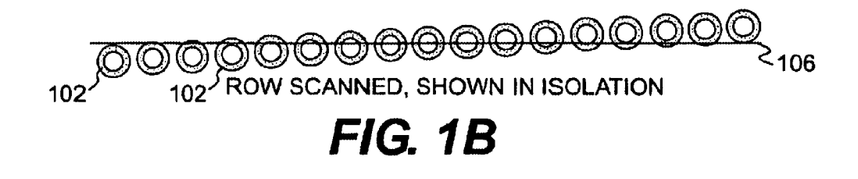
Figure 1C:
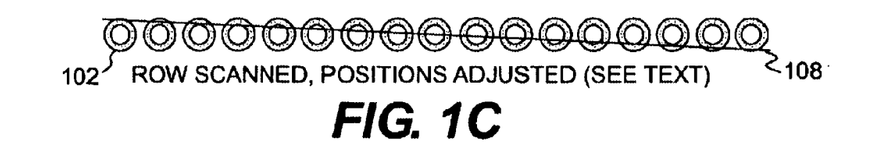
Figure 1D:
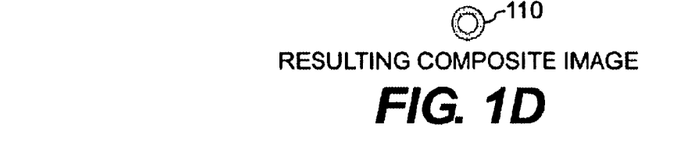

Any set of measurements, or rules describing measurements, that can be made on the individual annular elements 102 can be made just as well on the composite image 110. What is needed is a means, or method, by which those measurements and rules can be transformed into an algorithm that takes as its input the data in pixel form. The data that arises from a two-dimensional depiction of the pattern is all present in the one-dimensional data set.

Figure 2:
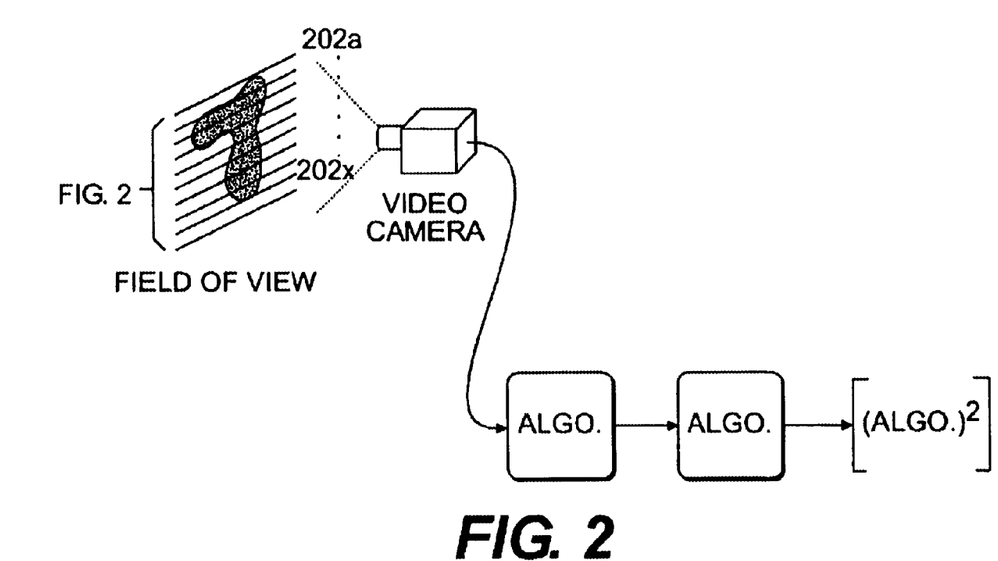
FIG. 2 illustrates how the inventive algorithm and system is applied to a two dimensional image without periodic elements.

FIG. 2 illustrates how the inventive system and algorithm is applied to a two-dimensional image 200 that does not have periodic elements. While two-dimensional image 200 in FIG. 2 does not include periodic elements, the process of scanning image 200 and converting it into an array of scan lines 202a–202x creates periodicity, whereby the periodicity is based on scan lines 202a–202x and not the elements in scan lines 202a–202x. In other words, two dimensional image 200 is a collection of one-dimensional images that are offset vertically from one another. Thereafter, the technique of search in the inventive algorithm is implemented against the array of periodic scan lines 202a–202x. The periodicity of the array of scan lines 202a–202x may contain slight variations that arise from the characteristic of the scanned image or from factors in the real world. Moreover, the electronic response of individual pixels is not very calibrated or precise, and there is a fair amount of variability or non-uniformity between even adjacent pixels in imaging arrays that are currently available. However, what the camera lacks in precision of individual pixels, it makes up for in the quantity of pixels used. The inventive algorithm thus analyzes many non-precise data to make precise determinations about an object by analyzing one-dimensional images of periodic subject matter. Thus, each scan line 202a–202x is one of the periodic elements and the length of each scan line 202a–202x is one period. Even if the image in each scan line 202a–202x is not periodic, the collection of scan lines is periodic, whereby the periodicity is imposed by the imaging device.

FIGS. 3 to 6 illustrate how the algorithm in the inventive method is implemented on a scan line with an array of periodic elements or on an array of periodic scan lines from a one-dimensional camera. The algorithm is essentially an application of a technique of search during analysis of run-length data that is derived from the array of periodic elements/scan lines.

Figure 3:
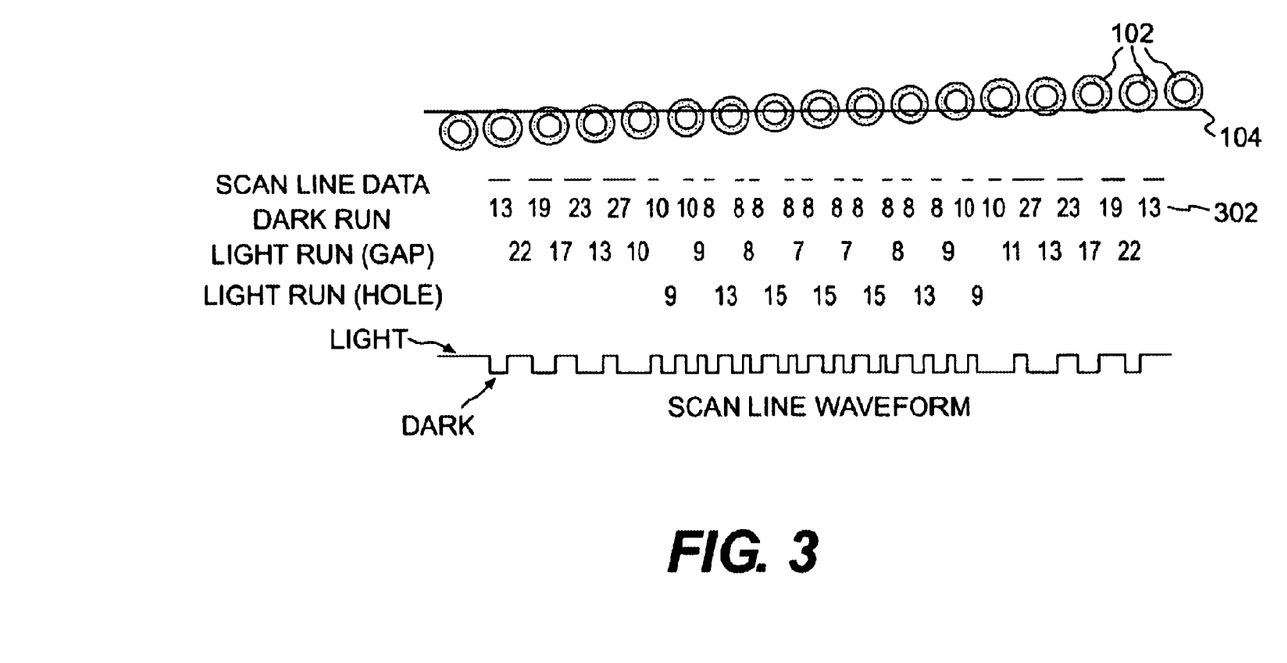
FIG. 3 illustrates a set of integers that results from the reduction of the scan line data.

FIG. 3 illustrates a set of integers 302 that results from the reduction of one scan line data with periodic elements. Integers 302 result from a collection of numbers each representing the brightness of a particular pixel, to "run-length encoded" data. The system reduces the scan line data to black and white images by determining if the data is darker or brighter than a predefined threshold. Thus, each pixel is reduced to a single bit in the computer. A consecutive set of all dark or white pixels in annular element/ring 102 through which horizontal line 104 passes is defined as a run. In FIG. 3 horizontal line 104 misses the first hole entirely so there is no run for this hole. The first run is a dark run with a length of 13, since horizontal line 104 passes through the dark section on top of the second hole. The next run is a light run with a length of 22, representing where horizontal line 104 passes through the gap between the second and third holes. It is these integers 302, i.e., 13, 22, 19, 17 . . . reading from left to right in FIG. 3, that are submitted as input to the algorithm in the inventive search method.

Figure 4:
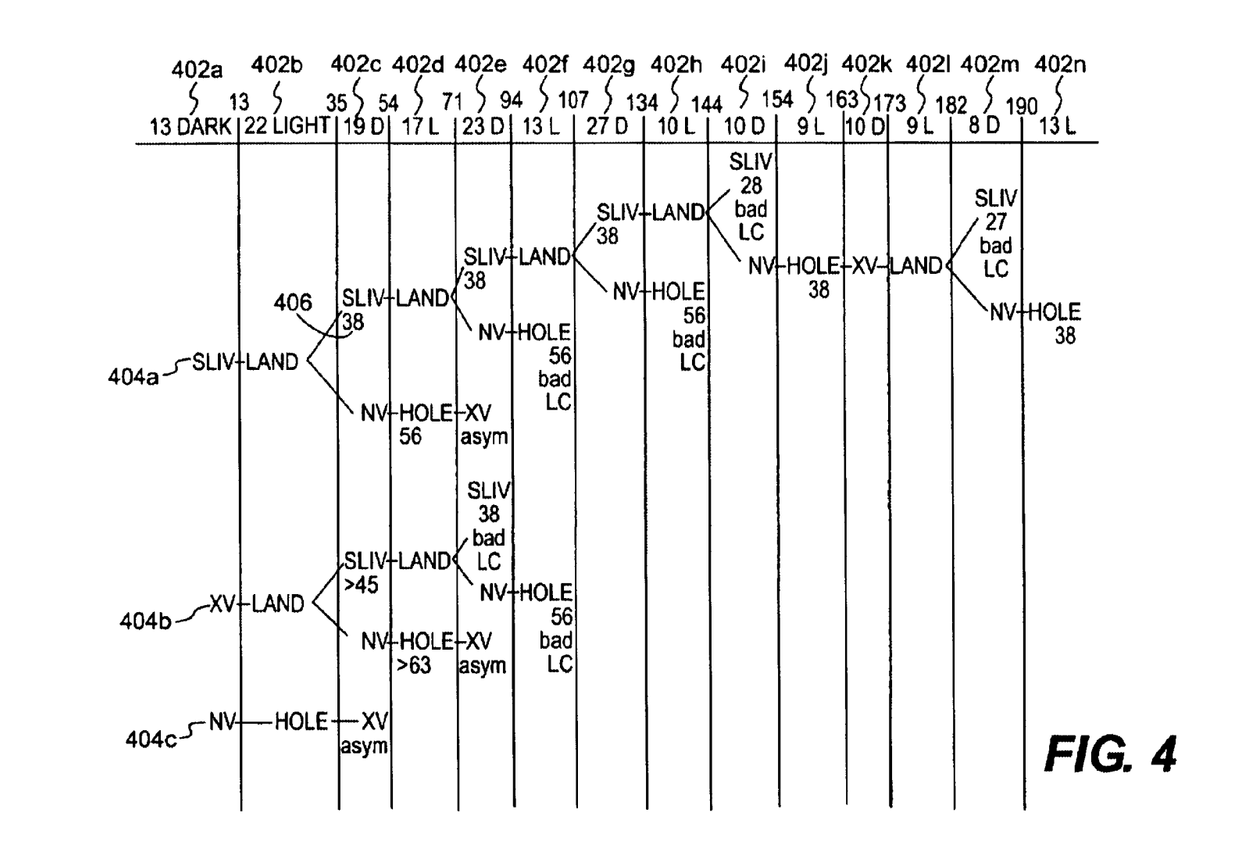
FIG. 4 illustrates the operation of the algorithm in the inventive method.

FIG. 4 illustrates a search tree for the first fourteen runs of the data in FIG. 3. In FIG. 4, a systematic accounting of every possible interpretation of each of the run-length integers 302 is made. Thus, columns 402a–402n each correspond to one run, whereby at the top of each column 402a–402n is the length of the run and a word or letter designating the run's illumination state as either "light", "L" or "dark", "D." For example, the first column's 402a heading is "13 Dark," because the first complete run shown in FIG. 3 is a dark run of length 13.

Figure 5:
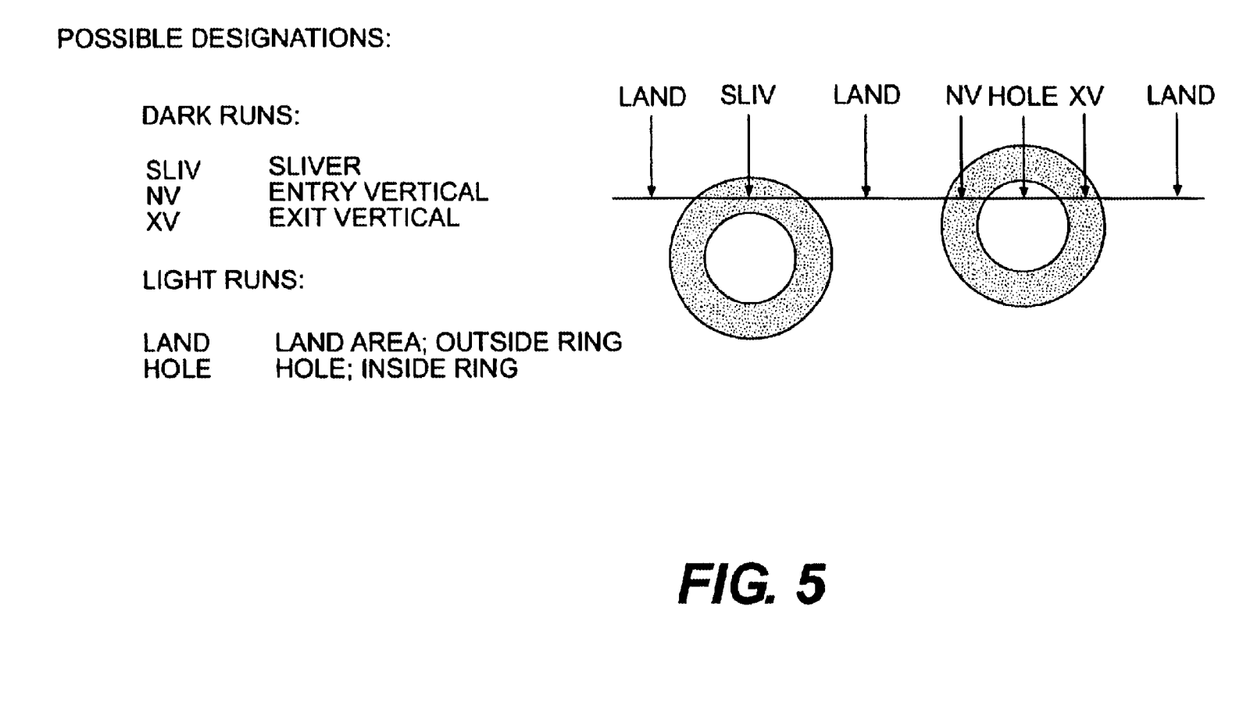
FIG. 5 illustrates symbolic designations under columns in FIG. 4.

FIG. 5 illustrates symbolic designations for each run. In an embodiment of the invention, symbolic designations under dark runs include a sliver (SLIV), an entry vertical (NV), and an exit vertical (XV). Symbolic designations under light runs include "LAND" and "HOLE". SLIV is the designation used when horizontal line 104 passes through the dark sections on the top or bottom of ring 102. Entry vertical is the designation used when horizontal line 104 passes through the dark section on the left of the center of ring 102. Exit vertical is the designation used when horizontal line 104 passes through the dark section on the right of the center of ring 102. HOLE is the designation used when horizontal line 104 passes through the light center of ring 102, and LAND is the designation used when horizontal line 104 passes through the light section outside of ring 102.

Referring back to FIG. 4, rows 404a–c represent possible interpretations of each run. For example, since the first run is a dark run, horizontal line 104 can only pass over the top or bottom sections (a SLIV run), the dark section on the left of the center (a NV run), or the dark section on the right of the center (a XV run). Thus, based on designations in the left column of each row, rows in FIG. 4 are used to create paths that account for every possible interpretation of each run. Upon interpreting each of run length integers 302, the "correct" path 404a, that is, the path that corresponds to the correct interpretation of the run-length data, is shown in bold print with heavy lines. The search technique implemented by the inventive algorithm is a systematic way of testing each interpretation and ignoring those interpretations that cannot be valid. When an interpretation is deemed to be invalid, any more extensive interpretation, of which this is only a part, is likewise invalid, and further processing power need not be expended to check it.

In FIG. 4, the annotations under some of the symbolic designations, particularly those that terminate a search path, show information that is discovered by interpreting the larger pattern of runs. For example, as soon as any path contains two SLIV runs, the lattice constant parameter may be estimated using a lattice constant rule. The lattice constant rule provides a method for calculating the lattice constant based upon the positions of the putative runs as tentatively identified in the systematic accounting. First a center point of the first SLIV or HOLE run is calculated by dividing the length of the run by two and rounding the decimal number to the next integer. By interpreting one path at a time, the rule adds the length of the first SLIV or HOLE run to the length of next run. The center point of the next SLIV or HOLE run is estimated by dividing the length of the run by 2, rounding up to the next integer and adding the quotient to the cumulative length. The center of the first SLIV or HOLE run, subtracted from the center of the second SLIV or HOLE run, equals the center-to-center distance, i.e., the distance between the first SLIV or HOLE run and the second SLIV or HOLE run. If there is discrepancy in the spacing between two SLIV and/or HOLE runs, analysis of the path is terminated under the lattice constant rule. This is because the center point of a SLIV or HOLE run must be at or close to the centerline of the annulus to which the SLIV or HOLE run belongs. Using the lattice constant rule, when a path has more than two HOLE or SLIV runs, more than one estimate of lattice constants can be made. If the estimated lattice constants are inconsistent with each other, that path contains an erroneous labeling and further interpretation of the path is terminated.

As shown in FIG. 4, the inventive system implementing the inventive method does not use brute force in analyzing each run, but instead uses a pattern rule based on the geometry of the targets and the lattice constant rule, whereby not all possibilities in the analysis work. An example of brute force analysis is testing all-possibilities of a run by making determinations, such as if a SLIV run is the first run, the next run has to be a LAND run and so on. The inventive method eliminates such brute force by terminating interpretations of paths rendered invalid by appropriate rules. In an embodiment of the invention, the method uses a symmetry rule for a circle. To illustrate how the circle rule is implemented, note at the bottom of column 402a, the method assumes that the run is a NV run. Thus, the next run must be a HOLE run and the following run must be an XV run. Upon analyzing the path, the entry vertical length is 13 and the exit vertical length is 19. Since the geometry of the hole is a circle, this path fails for asymmetry.

Using the lattice constant rule, for example in FIG. 4 path 404a, the method estimates the distance between previous runs. The SLIV run in column 402a, a dark run of length 13, has a center point of 6.5 which is thirteen divided by two. All decimal numbers in this rule are rounded to the next integer and so the center point of the first SLIV run is 7. The next run must be a LAND run, and analyzing along one path at a time, the following runs must be a SLIV run or an NV run. In FIG. 4, the numbers above the vertical lines represent a cumulative position. The number above the second vertical line, 35, represents the addition of the 13, the length of the first SLIV run, and 22, length of the light run in column 402b. The second SLIV run in that path has the center 45, which is the total of the quotient of 19, (the length of the dark run in column 402c, divided by 2 and rounded to the next integer) and added to 35 (the cumulative number from the top of the second vertical line). The center of the first SLIV run, 7, subtracted from the center of the second SLIV run, 45, equals to the center-to-center distance 406.

In FIG. 4, center-to-center distance 406 is the number represented under the second SLIV run, which in this case is 38. The next run in this path is a LAND run followed by a SLIV run and a NV run. Analyzing one path at a time, the run following the NV run has to be a HOLE run. The center of the HOLE is 101, i.e., the 13, the length of the run, divided by 2 and rounded up to the next integer plus 94 which is the cumulative length up to that HOLE. Using the lattice constant rule, a spacing calculation between the second SLIV run and the first HOLE run in this path shows a discrepancy. The spacing is 56, which is the center-to-center distance between the second SLIV and the HOLE. With the first spacing between the first and second SLIV runs estimated at 38, a spacing of 56 between the second SLIV run and the HOLE run does not correspond with the first spacing. Another spacing of 38 or a close number would be more acceptable. Thus, the lattice constant rule eliminates this path.

By using the pattern rule and the lattice constant rule, the algorithm can be used to analyze the pattern of rings in an array and to detect deviations from numerical acceptance norms, such as ring diameter, spacing, and symmetry for annular targets. Thus, the algorithm may be used to inspect a manufactured object where inspection of an array of annular ring for a defect is required.

Figure 6:
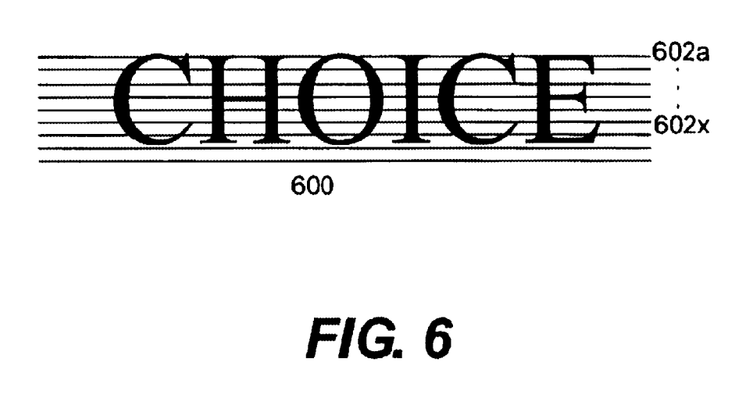
FIG. 6 illustrates how the rules used in the inventive algorithm can be applied to a two-dimensional image without periodic elements.

FIG. 6 illustrates an example of how the rules used in the inventive algorithm can be applied to a two-dimensional image 600 without periodic elements. While two-dimensional image 600 does not include periodic elements, the process of scanning image 600 and converting it into an array of scan lines 602a–602x creates periodicity, whereby the periodicity is based on scan lines 602a–602x and not the elements in scan lines 602a–602x. The rules that arise from the geometry of two-dimensional scene 600 involves a pattern order over a longer range. The first rule in the pattern order indicates that each letter gives rise to black and white areas in scan lines 602a–602x. Thus, as scan lines 602a–602x are imposed on image 600, each line includes dark and light areas. As each line 602a–602x is scanned into the system, the algorithm analyses the scan line 602a–602x based on information from previously scanned lines and the current scan line. The algorithm eliminates all invalid interpretation. For example, the top of the "C" may be interpreted as a "C" or "S" or another letter with a curve top and the algorithm eliminates letters such as "Z" with a flat top. The system stores this information and analyzes the next line. The algorithm uses this analysis and the set of all approximate measurements about image 600 to obtain the exact nature of image 600 in a larger context. The algorithm thus serves as a syntax validator for determining whether a certain interpretation makes sense under predetermined rules. An invalid syntax corresponds with a flaw in the object and a valid interpretation corresponds to a correct interpretation.

As would be apparent to those of ordinary skill in the art, rules used in the inventive method may be modified as long as there are enough defined rules to keep the sorting tree from growing without bound. This makes the inspection problem computable, that is, paths can be computed in parallel by multiple simple processors at very high speed. Using relatively cheap chips that can be programmed with AND gates and OR gates, a system implementing the inventive method can easily perform 100 billion operations per second. Thus, the method is expressible as a custom or semi-custom integrated circuit chip and can scale well to a highly parallel implementation. Moreover the path-analysis method works even in the presence of considerable noise and other real-world imperfections. The inventive algorithm can be extended for use with slot-shaped holes, which appear as oval targets in the video image. The algorithm has shown the capacity to distinguish automatically between circular and slot-shaped holes.

The foregoing description has been directed to specific embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A method in a system for using electronically acquired imagery of an object to inspect the object for a wide variety of manufacturing defects, the method comprising the steps of:

capturing, by a capturing means, an image of the object and converting the image into an array of periodic elements;

delivering the array of periodic elements to a computer system for sequencing;

reducing each periodic element into segments consisting of sets of similar adjacent pixels;

systematically accounting for all possible interpretations of each run using a plurality of predefined rules to determine deviations from a set of acceptance norms for the array of periodic elements; and systematically testing each interpretation wherein invalid interpretations are ignored.

2. The method of claim 1, wherein the step of converting further comprises the step of converting a one-dimensional image of the object into a scan line with an array of periodic elements.

3. The method of claim 1, wherein the step of converting further comprises the step of converting a two-dimensional image of the object into an array of periodic scan lines, whereby the length of each scan line is one period.

4. The method of claim 1, wherein the step of reducing further comprises the steps of:

defining a run as a consecutive set of all dark or light pixels in the array of periodic elements;

creating a collection of integers, each representing brightness of similar adjacent pixels in a run-length encoded data;

breaking down the periodic elements into segments, whereby each segment comprises sets of adjacent pixels that are similar in brightness or hue or similar in brightness and hue; and representing each segment with one of a plurality of run-length integers.

5. The method of claim 4, wherein the step of systematically accounting further comprises the step of assigning a symbolic designation to each run of the periodic element by:

a. designating a dark run as a sliver run when a horizontal line passes through dark sections on top or bottom of an annular element in the array of periodic elements;

b. designating the dark run as an entry vertical run when the horizontal line passes through dark sections on a left of a center of the annular element;

c. designating the dark run as an exit vertical run when the horizontal line passes through dark sections on a right of the center of the annular element;

d. designating a light run as a HOLE run when the horizontal line passes through a light center of the annular element; and e. designating the light run as a LAND run when the horizontal line passes through a light section between two annular elements.

6. The method of claim 5, wherein the step of systematically accounting further comprises the step of applying each run to a search tree table having rows and columns and systematically accounting for every possible interpretation of each of the plurality of run-length integers.

7. The method of claim 6, wherein the step of systematically accounting further comprises the steps of:

corresponding each run to a column in the search tree table, whereby a top of each column shows a length of the run and a word or letter designating an illumination state of the run as either light or dark;

corresponding each interpretation of a run to a row in the search tree table;

basing designations of a current column, in the interpretation path, on the designation in a previous column in the same interpretation path;

estimating a lattice constant parameter, using a lattice constant rule, as soon as the interpretation path contains two sliver runs; and estimating a lattice constant parameter, using a lattice constant rule, as soon as the interpretation path contains two hole runs.

8. The method of claim 7, wherein the step for estimating the lattice constant parameter comprises the steps of:

calculating a first center point of the first sliver run or the first hole run by dividing the length of the first sliver run or the first hole run by two and rounding to a next integer;

adding the length of the first sliver run or the first hole run to the length of the next run in an interpretation path;

calculating a second center point of a second sliver run or a second hole run by dividing the length of the second sliver run or the second hole run by two, rounding to a second integer and adding the second integer to the length of a cumulative length of all preceding runs in a path;

subtracting the first center point from the second center point; and determining if there is discrepancy in spacing between two sliver runs or two hole runs and terminating the interpretation path if there is discrepancy.

9. The method of claim 1, wherein the step of reducing further comprises the step of identifying every segment to determine what features of the object the segment and periodic element represent.

10. The method of claim 9, wherein the step of identifying further comprises the step of automatically resolving a physical object into finite elements for stress or thermal analysis.

11. The method of claim 9, wherein the step of identifying every segment comprises the step of locating at least one set of labels, in which every segment in the periodic element has at least one label that defines the segment.

12. The method of claim 1, wherein the step of reducing further comprises the step of reducing data in the array of periodic elements to black and white images by determining if the data is darker or brighter than a predefined threshold and reducing each pixel to a single bit in the system.

13. The method of claim 1, wherein the step of reducing further comprises the step of reducing data in the scan line to non-binary format whereby the data is reduced to multiple bits.

14. The method of claim 1, wherein the step of reducing further comprises the steps of:

defining a run as a light run if a horizontal line passes through a light part of the periodic element; and defining a run as a dark run if the horizontal line passes through a dark part of the periodic element.

15. The method of claim 1, wherein the step of reducing further comprises the steps of:

using a lattice constant rule for measuring spacing between the periodic elements in the array whereby a lattice constant is measured without prior knowledge of the array of periodic elements being observed;

using an inference rule; or using a pattern rule that is derived from a geometry of the periodic elements.

16. A system for using electronically acquired imagery of an object to inspect the object for a wide variety of manufacturing defects, the system comprising:

a capturing means for electronically capturing an image of the object and converting the image into an array of periodic elements;

means for delivering the array of periodic elements from the capturing means to a computer system; and software means in the computer system for processing and reducing the array of periodic elements to a plurality of run-length integers whereby each run-length integer represents one run, systematically accounting for all possible interpretations of each run using a plurality of predefined rules to determine deviations from a set of acceptance norms for the array of periodic elements, systematically testing each interpretation, and ignoring invalid interpretations.

17. The system of claim 16, wherein the capturing means is a camera.

18. The system of claim 16, wherein the capturing means is a scanning device.

19. The system of claim 16, wherein the array of periodic elements is an array of periodic scan lines from a two-dimensional image.

20. The system of claim 16, wherein the array of periodic elements is an array of geometrically similar elements.

21. The system of claim 16, wherein means for delivering the scan line is performed in the capturing means in conjunction with other ancillary electronic data processing means.

22. The system of claim 16, wherein the software means:

defines a run as a consecutive set of all dark or light pixels in the array of periodic elements;

creates a collection of numbers, each representing brightness of a particular pixel in a run-length encoded data;

breaks down the periodic elements into segments, whereby each segment comprises sets of adjacent pixels that are similar in brightness or hue or similar in brightness and hue;

represents each segment with one of a plurality of run-length integers; and identifies every segment by locating at least one set of labels in which every segment in the periodic element has at least one label that defines the segment.

23. The system of claim 22, wherein the software means:

reduces data in a periodic element to black and white images by determining if the data is darker or brighter than a predefined threshold and reducing each pixel to a single bit in the system; or reduces data in a scan line to non-binary format whereby the data is reduced to multiple bits.

24. The system of claim 23, wherein the software means:

defines the run as a light run if a horizontal line passes through a light part of the periodic element; and defines the run as a dark run if the horizontal line passes through a dark part of the periodic element.

25. The system of claim 16, wherein the predefined rules comprises:

a lattice constant rule for measuring spacing between the periodic elements in the array, whereby a lattice constant is measured without prior knowledge of the scan line being observed;

an inference rule; and a pattern rule that is derived from a geometry of the periodic elements.

26. The system of claim 25, wherein the software means applies each run to a search tree table having rows and columns and systematically accounts for every possible interpretation of each of the plurality of run-length integers by creating an interpretation path in the search tree table for each interpretation.

27. The system of claim 26, wherein the software means:
   corresponds each run to a column in the search tree table, whereby a top of each column shows a length of the run and a word or letter designating illumination state of the run as either light or dark;
   corresponds each interpretation of a run to a row in the table; and
   bases designations of a current column, in an interpretation path, on designation of a previous column in the same interpretation path.

28. The system of claim 16, wherein the software means assigns a symbolic designation to each run by:
   designating a dark run as a sliver run when a horizontal line passes through dark sections on top or bottom of an annular element in the array of periodic elements;
   designating the dark run as an entry vertical run when the horizontal line passes through dark sections on a left of a center of the annular element;
   designating the dark run as an exit vertical run when the horizontal line passes through dark sections on a right of the center of the annular element;
   designating a light run as a HOLE run when the horizontal line passes through a light center of the annular element; and
   designating the light run as a LAND run when the horizontal line passes through a light section between two annular elements.

29. The system of claim 28, wherein as soon as the interpretation path contains two sliver runs or two hole runs, a lattice constant parameter is estimated using a lattice constant rule whereby the lattice constant rule is used to estimate the distance between previous runs in the path, the lattice constant parameter is estimated by:
   a. calculating a first center point of a first sliver run or a first hole run by dividing the length of the first sliver run or the first hole run by two and rounding to a first integer;
   b. adding the length of the first sliver run or the first hole run to the length of the next run in an interpretation path;
   c. calculating a second center point of a second sliver run or a second hole run by dividing the length of the second sliver run or the second hole run by two, rounding to a second integer and adding the second integer to the length of a cumulative length of all preceding runs in a path;
   d. subtracting the first center point from the second center point; and
   e. determining if there is discrepancy in spacing between two sliver runs or two hole runs and terminating the interpretation if there is discrepancy.

30. A software component in a computer system for inspecting electronically acquired imagery of an object for a wide variety of manufacturing defects, the software component comprising:
   first processing mean for processing and reducing an array of periodic elements to a plurality of run-length integers whereby each run-length integer represents one run;
   second processing means for systematically accounting for all possible interpretations of each run using a plurality of predefined rules to determine deviations from a set of acceptance norms for the array of periodic elements; and
   third processing means for systematically testing each interpretation and for ignoring invalid interpretations.

31. The software component of claim 30, wherein the first processing means:
   defines a run as a consecutive set of all dark or light pixels in the array of periodic elements;
   creates a collection of numbers, each representing the brightness of a particular pixel in a run-length encoded data;
   breaks down the periodic elements into segments, whereby each segment comprises sets of adjacent pixels that are similar in brightness or hue or similar in brightness and hue;
   represents each segment with one of a plurality of run-length integers; and
   identifies every segment by locating at least one set of labels in which every segment in the periodic element has at least one label that defines the segment.

32. The software component of claim 30, wherein the first processing means:
   reduces data in a periodic element to black and white images by determining if the data is darker or brighter than a predefined threshold and reducing each pixel to a single bit in the system; or
   reduces data in the periodic element to non-binary format whereby the data is reduced to multiple bits.

33. The software component of claim 32, wherein the first processing means:
   defines the run as a light run if a horizontal line passes through a light part of a geometric element in the array of periodic elements; and
   defines the run as a dark run if the horizontal line passes through a dark part of the geometric element.

34. The software component of claim 30, wherein the predefined rules comprises:
   a lattice constant rule for measuring spacing between the geometric elements in the array, whereby a constant can be measured without prior knowledge of the scan line being observed;
   an inference rule for analyzing a two-dimensional image; and
   a pattern rule that is derived from the geometry of the geometric elements.

35. The software component of claim 30, wherein the second processing means assigns a symbolic designation to each run by:
   designating a dark run as a sliver run when a horizontal line passes through dark sections on top or bottom of an annular element in the array of periodic elements;
   designating the dark run as a entry vertical run when the horizontal line passes through dark sections on a left of a center of the annular element;
   designating the dark run as an exit vertical run when the horizontal line passes through dark sections on a right of the center of the annular element;
   designating a light run as a HOLE run when the horizontal line passes through a light center of the annular element; and
   designating the light run as a LAND run when the horizontal line passes through a light section between two annular elements.

36. The software component of claim 30, wherein the third processing means applies each run to a search tree table having rows and columns and systematically accounts for every possible interpretation of each of the plurality of run-length integers by creating an interpretation path in the search tree table for each interpretation.

37. The software component of claim 36, wherein the third processing means:
- corresponds each run to a column in the search tree table, whereby the top of each column shows a length of the run and a word or letter designating an illumination state of the run as either light or dark;
- corresponds each interpretation of a run to a row in the table; and
- bases designations for a current column, in the interpretation path, on designation in a previous column in the same interpretation path.

38. The software component of claim 37, wherein as soon as the interpretation path contains two sliver runs or two hole runs, a lattice constant parameter is estimated using a lattice constant rule whereby the lattice constant rule is used to estimate the distance between previous runs in the path, the lattice constant parameter is estimated by:
- a. calculating a first center point of a first sliver run or a first hole run by dividing the length of the first sliver run or the first hole run by two and rounding to a first integer;
- b. adding the length of the first sliver run or the first hole run to the length of the next run in the interpretation path;
- c. calculating a second center point of a second sliver run or the second hole run by dividing the length of the second sliver run or the second hole run by two, rounding to a second integer and adding the second integer to a cumulative length of all preceding runs in a path;
- d. subtracting the first center point from the second center point; and
- e. determining if there is discrepancy in the spacing between two sliver runs or two hole runs and terminating the interpretation if there is discrepancy.

39. A system for using electronically acquired imagery of an object to inspect the object for a wide variety of manufacturing defects, the system comprising:
- a capturing means for electronically capturing an image of the object and converting the image into an array of periodic elements;
- means for delivering the array of periodic elements from the capturing means to a computer system;
- software means in the computer system for processing and reducing the array of periodic elements to a plurality of run-length integers whereby each run-length integer represents one run, for systematically accounting for all possible interpretations of each run using a plurality of predefined rules to determine deviations from a set of acceptance norms for the array of periodic elements, systematically testing each interpretation, and ignoring invalid interpretations; and
- a plurality of simple processors for parallel processing of a plurality of interpretations at very high speed.

* * * * *